US009026421B2

(12) United States Patent
Tao et al.

(10) Patent No.: US 9,026,421 B2
(45) Date of Patent: May 5, 2015

(54) METHOD OF MODELING CLOUD POINT OF A MIXTURE OF FATTY ACID METHYL ESTERS USING A MODIFIED UNIFAC MODEL AND A SYSTEM THEREFOR

(75) Inventors: Bernard Y Tao, Lafayette, IN (US); Junli Liu, Riverside, CA (US)

(73) Assignee: Purdue Research Foundation, West Lafayette, IN (US)

( * ) Notice: Subject to any disclaimer, the term of this patent is extended or adjusted under 35 U.S.C. 154(b) by 234 days.

(21) Appl. No.: 13/566,755

(22) Filed: Aug. 3, 2012

(65) Prior Publication Data

US 2013/0204591 A1    Aug. 8, 2013

Related U.S. Application Data

(60) Provisional application No. 61/573,012, filed on Aug. 3, 2011.

(51) Int. Cl.
*G06G 7/48* (2006.01)
*G06F 17/50* (2006.01)
*C10L 1/19* (2006.01)
*C07C 57/12* (2006.01)
(Continued)

(52) U.S. Cl.
CPC ............... *G06F 17/5009* (2013.01); *C10L 1/19* (2013.01); *C07C 57/12* (2013.01); *C07C 53/126* (2013.01); *G06F 19/704* (2013.01)

(58) Field of Classification Search
CPC ............ A01C 1/00; A01C 1/06; A01N 25/26; A23D 7/00; A23D 9/00; A23K 1/00; A23L 1/20; B32B 5/18; C07C 53/00; C07C 53/126; C07C 57/12; C07H 21/04; C07K 21/04; C08F 4/64; C09K 5/00; C09K 5/02; C09K 21/02; C09K 21/04; C10L 1/18; C10L 1/188; C10L 1/19; C11C 5/00; C11D 3/22; C11D 3/39; C11D 17/00; C12N 5/04; C12N 9/04; C12N 15/09; C12N 15/81; C12N 15/82; C12N 15/63; C12P 7/58; C12P 7/64; C12P 21/02; E04B 2/34; E04B 2/86; E04C 2/04; E04C 2/20; E04C 2/22; E04C 2/28; F23D 15/00; G06F 17/50
USPC ................................. 703/12; 44/385; 800/312
See application file for complete search history.

(56) References Cited

U.S. PATENT DOCUMENTS

| | | | | |
|---|---|---|---|---|
| 6,426,448 B1 * | 7/2002 | Booth et al. | ................... | 800/312 |
| 2004/0049813 A1 * | 3/2004 | Russell et al. | ................. | 800/312 |
| 2011/0023352 A1 * | 2/2011 | Knuth et al. | ..................... | 44/385 |

OTHER PUBLICATIONS

Dunn, R.O., "Crystallization behavior of Fatty Acid Methyl Esters", Journal of American Oil Chem Society, 2008.*

(Continued)

*Primary Examiner* — Kandasamy Thangavelu
(74) *Attorney, Agent, or Firm* — Purdue Research Foundation

(57) ABSTRACT

A method for predicting onset of liquid phase to solid phase transition of a mixture including a plurality of fatty acid methyl esters components. The method includes identifying chemical and molecular structure of each component of the mixture, calculating activity coefficients for each component in a liquid phase and a solid phase, calculating chemical potential for each component in the liquid phase and in the solid phase at a predetermined temperature and a predetermined pressure, and calculating the cloud point of the mixture. A system for carrying out the method is also disclosed.

1 Claim, 8 Drawing Sheets

(51) Int. Cl.
    C07C 53/126      (2006.01)
    G06F 19/00       (2011.01)

(56) References Cited

OTHER PUBLICATIONS

Chang et al., "Integrated process modeling and product design of biodiesel manufacturing", Industrial Engineering Chemical Research, 2010.*

Alcantara, et al. "Catalytic production of biodiesel from soy-bean oil, used frying oil and tallow," Biomass and Bioenergy, 2000, vol. 18, No. 6; pp. 515-527.

Bailey, et al. "Solubilities of some normal saturated and unsaturated long-chain fatty acid methyl esters in acetone, n-hexane, toluene, and 1,2-dichloroethane," Journal of Chemical & Engineering Data, 1970, vol. 15, No. 4; pp. 583-585.

Benjumea, et al. "Basic properties of palm oil biodiesel-diesel blends," Fuel, 2008, vol. 87, No. 10; pp. 2069-2075.

Bhale, et al. "Improving the low temperature properties of biodiesel fuel," Renewable Energy, 2009, vol. 34, No. 3; pp. 794-800.

Boey, et al. "Biodiesel production via transesterification of palm olein using waste mud crab (*Scylla serrata*) shell as a heterogeneous catalyst," Bioresource Technology, 2009, vol. 100, No. 24; pp. 6362-6368.

BP, "BP Statistical Review of World Energy Jun. 2011," BP p.l.c., London, 2011.

Cetinkaya, et al. "Optimization of Base-Catalyzed Transesterification Reaction of Used Cooking Oil," Energy & Fuels, 2004, vol. 18, No. 6; pp. 1888-1895.

Cheng Sit Foon, et al. "Crystallisation and Melting Behavior of Methyl Esters of Palm Oil," American Journal of Applied Sciences, 2006, vol. 3, No. 5; pp. 1859-1863.

Chiu, et al. "Impact of cold flow improvers on soybean biodiesel blend," Biomass and Bioenergy, 2004, vol. 27, No. 5; pp. 485-491.

Dantas, et al. "Characterization and kinetic compensation effect of corn biodiesel," Journal of Thermal Analysis and Calorimetry, 2007, vol. 87, No. 3; pp. 847-851.

Demirbas, "Biodiesel from waste cooking oil via base-catalytic and supercritical methanol transesterification," Energy Conversion and Management, 2009, vol. 50, No. 4; pp. 923-927.

Dias, et al. "Production of biodiesel from acid waste lard," Bioresource Technology, 2009, vol. 100, No. 24; pp. 6355-6361.

Diaz-Felix, et al. "Pretreatment of yellow grease for efficient production of fatty acid methyl esters," Biomass and Bioenergy, 2009, vol. 33, No. 4; pp. 558-563.

Dizge, et al. "Biodiesel production from sunflower, soybean, and waste cooking oils by transesterification using lipase immobilized onto a novel microporous polymer," Bioresource Technology, 2009, vol. 100, No. 6; pp. 1983-1991.

Dunn, et al. "Low-Temperature Properties of Triglyceride-Based Diesel Fuels: Transesterified Methyl Esters and Petroleum Middle Distillate/Ester Blends," JAOCS, 1995, vol. 72, No. 8; pp. 895-904.

Dunn, "Effects of Minor Constituents on Cold Flow Properties and Performance of Biodiesel," Progress in Energy and Combustion Science, 2009, vol. 35, No. 6; pp. 481-489.

Dunn, et al. "Low-Temperature Filterability Properties of Alternative Diesel Fuels from Vegetable Oils," Fuel and Energy Abstracts, 1997, vol. 38, No. 5.

Dunn, et al. "Improving the Low-Temperature Properties of Alternative Diesel Fuels: Vegetable Oil-Derived Methyl Esters," JAOCS, 1996, vol. 73, No. 12; pp. 1719-1728.

* cited by examiner

METHOD OF MODELING CLOUD POINT OF A MIXTURE OF FATTY ACID METHYL ESTERS USING A MODIFIED UNIFAC MODEL AND A SYSTEM THEREFOR

The present U.S. Non-provisional patent application is related to and claims the priority benefit of U.S. Provisional Patent Application Ser. No. 61/573,012, filed Aug. 3, 2011, the contents of which is hereby incorporated by reference in its entirety into this disclosure.

TECHNICAL FIELD

The present disclosure generally relates to Fatty Acid Methyl Esters (FAME), and in particular to processing of FAME for use as a constituent of biodiesel.

BACKGROUND

Biodiesel is viewed as the alternative fuel to the petroleum diesel due to the renewable and environmental friendly properties. Biodiesel is a mixture of fatty acid methyl esters (FAME) produced from vegetable oils/animal fats by trans-esterification with methanol as well as other constituents. The compositions of FAME are constrained by the feedstock of vegetable oils/animal fats. There are six main types of FAME in biodiesel: methyl palmitate (C16:0), methyl palmitoleate (C16:1), methyl stearate (C18:0), methyl oleate (C18:1), methyl linoleate (C18:2) and methyl linolenate (C18:3); however, there may be other components known to a person having ordinary skill in the art.

The compositions of the FAME significantly affect the cold flow properties. Cold flow properties are the performances of biodiesel at low temperature. Cold flow properties of FAME can be characterized by cloud point, pour point, cold filter plugging point, and low temperature filterability test. Moreover, in North America, cloud point is used as the most appropriate standard to characterize the cold flow properties of FAME. Cloud point is referred as the temperature when biodiesel starts to form crystals (when phase separation begins to appear (i.e., when the mixture becomes "cloudy") and the thickening fluid can clog filters or other orifices). According to the definition of cloud point, cloud point show FAME change from pure liquid mixture to liquid/solid mixtures. Therefore, cloud point is a phenomenon of solid-liquid equilibrium. The cloud point of FAME depends on the composition because the main FAME components have different melting points (as shown in Table 1). The mixture of FAME with high level of high melting point components will result in a high cloud point.

TABLE 1

Melting point of substantially pure FAME components

| Components | Melting point (° C.) |
|---|---|
| C16:0 | 30 |
| C16:1 | 0.5 |
| C18:0 | 38 |
| C18:1 | −20 |
| C18:2 | −35 |
| C18:3 | −52 |

The quantitative relationship between the composition of FAME and cloud point is known. For example, Liu et al. have established the quantitative relationship between the composition of FAME and the cloud point through multiple linear statistical regression. This quantitative model shows fatty acid methyl esters with high melting points have more significant effect than those with low melting points. However, the prediction model is challenged due to a low value of $R^2$ (proportion of variability in a data set based on how well future outcomes are predicted by a model). Imahara et al. use the thermodynamic phase heterogeneous equilibrium principal to predict the cloud point of fatty acid methyl esters according to the fraction of high melting point component. This prediction model is also challenged because the interaction between the components is not considered. Boros et al. used the thermodynamic model to predict the cloud point of fatty acid methyl esters with the UNIQUAC (UNIversal QUAsiChemical is an activity coefficient model used in description of phase equilibria) to predict the non-ideal behavior and as a result the predictability of the model significantly improved. However, their model is also challenged since it needs to be provided various parameters when a new component is added into a mixture.

While UNIFAC (UNIversal Functional Activity Coefficient) models (see Zhong, Sato, Masuoka, and Chen) have been used for predicting liquid-vapor transitions, the UNIFAC model or the modified UNIFAC model (see Gmehling, Li, and Schiller; Lohmann & Gmehling; Lohmann, Röpke, and Gmehling; Weidlich and Gmehling; and Wittig, Lohmann, and Gmehling) has not been used for predicting liquid-solid transition.

A basic challenge, therefore, remains. Specifically, when various components of fatty acid methyl esters from different sources are added, predicting the cloud point of the new mixture remains a challenge. This challenge is especially problematic since fatty acid methyl esters can originate from many sources. In fact the number of sources from which FAME can originate from may be more diverse than sources of fossil fuel. Furthermore, there can be various additives that can be included in the overall composition. Each of these presents a significant challenge for predicting the cloud point of the mixture.

Therefore, in light of the foregoing challenges with cloud point prediction, a method and a system for accurately predicting cloud point in a mixture of fatty acid methyl esters is needed where the method utilizes molecular interactions between the esters and the relationship therebetween to further provide accuracy to the prediction.

SUMMARY

The present disclosure provides a method for predicting onset of liquid phase to solid phase transition of a mixture including a plurality of fatty acid methyl esters components. The method includes identifying chemical and molecular structure of each component of the mixture. The method further includes calculating activity coefficients for each component in a liquid phase and a solid phase. The method also includes calculating chemical potential for each component in the liquid phase and in the solid phase at a predetermined temperature and a predetermined pressure. The method further includes calculating the cloud point of the mixture.

DETAILED DESCRIPTION

Figure 1:
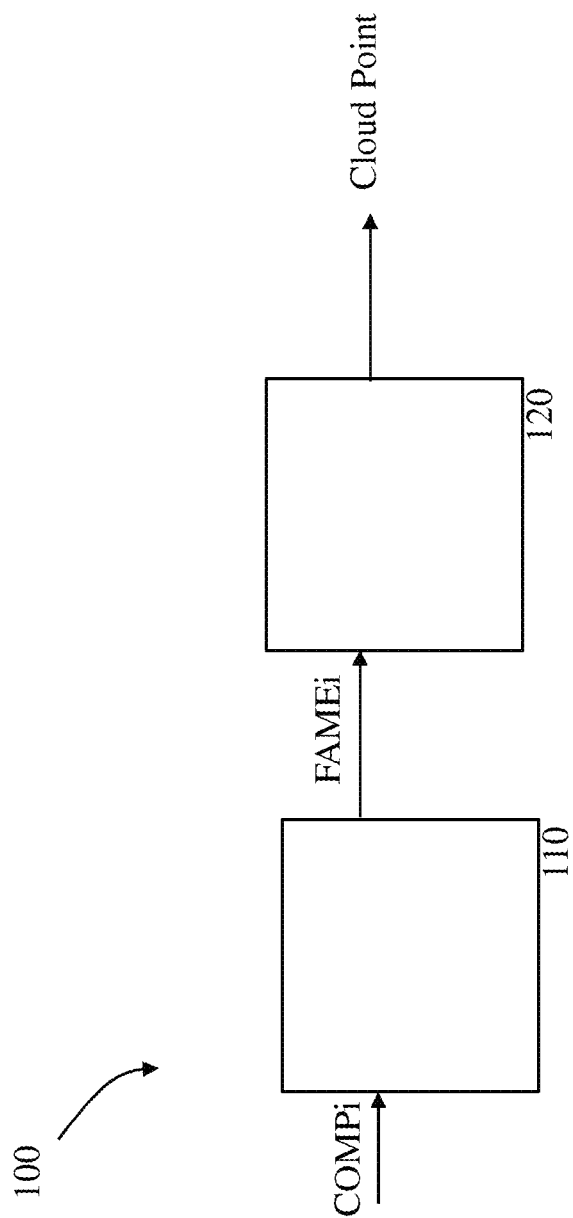
FIG. 1 is a schematic of a system for detecting components of a mixture and predicting the cloud point of the mixture.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel method and system have been developed for predicting cloud point in a mixture including fatty acid methyl esters (FAME). The system 100 is depicted in FIG. 1. In the system 100, a component detection unit 110; e.g. a mass spectrometer (i.e., a unit which uses masses of particles for determining the elemental composition of a sample) is coupled to a cloud point modeling unit 120. The component detection unit 110 is configured to receive samples (identified as $COMP_i$ in FIG. 1, referring to multiple samples from components of a mixture, e.g., a biodiesel mixture) sequentially. The samples are analyzed by the component detection unit 110 and molecular information of each component is provided to the cloud point modeling unit 120. The cloud point modeling unit 120 is configured to receive molecular information (identified as $FAME_i$ in FIG. 1, indicating sequential transfer of molecular information associated with each component $COMP_i$) from the component detection unit 110 and further configured to use the method outlined below to predict the cloud point of a mixture that includes the components. It should be appreciated that parts of the system depicted in FIG. 1 can be operated sequentially or in a parallel fashion. For example, a sample of the mixture intended to form the biodiesel mixture can be provided to the component detection unit 110 as a single sample, and the component detection unit 110 can provide molecular information about individual components of the mixture to the cloud point modeling unit 120 in a sequential manner.

Prediction of Cloud Point

To describe the cloud point modeling methodology, a theoretical description of molecular interaction is provided herein.

Phase Equilibrium in the Heterogeneous Closed System

For a closed system with n phases and m components, at equilibrium, there exist the following relations:

(1) The temperature in each phase is the same:

$$T_1=T_2=\ldots=T_n=T \quad \text{Eq. 1}$$

(2) The pressure in each phase is the same:

$$P_1=P_2=\ldots=P_n=P \quad \text{Eq. 2}$$

(3) The chemical potential (i.e., partial molar free energy, is a form of potential energy that can be absorbed or released during a chemical reaction) of component i in each phase (i.e., liquid and solid) is the same:

$$\mu_i^1=\mu_i^2=\ldots=\mu_i^n=\mu_i \quad \text{Eq. 3}$$

The chemical potential of each component i is represented by:

$$\mu_i(T,P)=\mu_i^o(T,P)+RT\ln(\alpha_i) \quad \text{Eq. 4}$$

Where
$\mu_i^o$: Standard chemical potential at temperature T and pressure P
R: gas constant with the value of 8.3145 J·mol$^{-1}$·K$^{-1}$
T: is the temperature
$\alpha_i$: Activity of component i
The chemical potential of A in phase 1 and phase 2 are shown in 5 and 6, respectively.

$$\mu_A^1(T,P)=\mu_A^{1,o}(T,P)+RT\ln(\alpha_A^1) \quad \text{Eq. 5}$$

Where
$\mu_A^1(T,P)$: Chemical potential of A in phase 1 at temperature T and pressure P
$\mu_A^{1,o}(T,P)$: Standard chemical potential of A in phase 1 at temperature T and pressure P
$\alpha_A^1$: Activity of A in phase 1

$$\mu_A^2(T,P)=\mu_A^{2,o}(T,P)+RT\ln(\alpha_A^2) \quad \text{Eq. 6}$$

Where
$\mu_A^2(T,P)$: Chemical potential of A in phase 2 at temperature T and pressure P
$\mu_A^{2,o}(T,P)$: Standard chemical potential of A in phase 2 at temperature T and pressure P
$\alpha_A^2$: Activity of A in phase 2

When A in phase 1 and phase 2 are in an equilibrium state, the chemical potential of A in each phase is the same. Therefore, Eq. 5 and Eq. 6 can be combined into Eq. 3, as provided below in Eq. 7.

$$\mu_A^{1,o}(T,P)RT\ln(\alpha_A^1)=\mu_A^{2,o}(T,P)RT\ln(\alpha_A^2) \quad \text{Eq. 7}$$

The relationship between the activity of A in phase 1 and phase 2 is shown in Eqs. 8 and 9.

$$RT\ln(\alpha_A^1/\alpha_A^2)=\Delta\mu_A^o(T,P) \quad \text{Eq. 8}$$

$$\Delta\mu_A^o(T,P)=\mu_A^{2,o}(T,P)-\mu_A^{1,o}(T,P) \quad \text{Eq. 9}$$

Where
$\Delta\mu_A^o(T,P)$: Standard chemical potential change of A from phase 1 to 2

Therefore, according to condition of heterogeneous phase equilibrium and the definition of chemical potential, Eqs. 8 and 9 can be written in the form of Eq. 9A.

$$RT\ln\left(\frac{\gamma_i^S x_i^S}{\gamma_i^L x_i^L}\right)=\mu_i^{0,L}(T,P)-\mu_i^{0,S}(T,P) \quad \text{Eq. 9A}$$

The chemical potential cannot be readily calculated; however, it can be calculated according the following relationship (as shown in Eq. 10).

$$\Delta\mu_A^o(T,P)=\Delta H_m-T\Delta S_m \quad \text{Eq. 10}$$

Where
$\Delta H_m$: Enthalpy change of A from phase 1 to 2
$\Delta S_m$: Entropy change of A from phase 1 to 2

Figure 2:
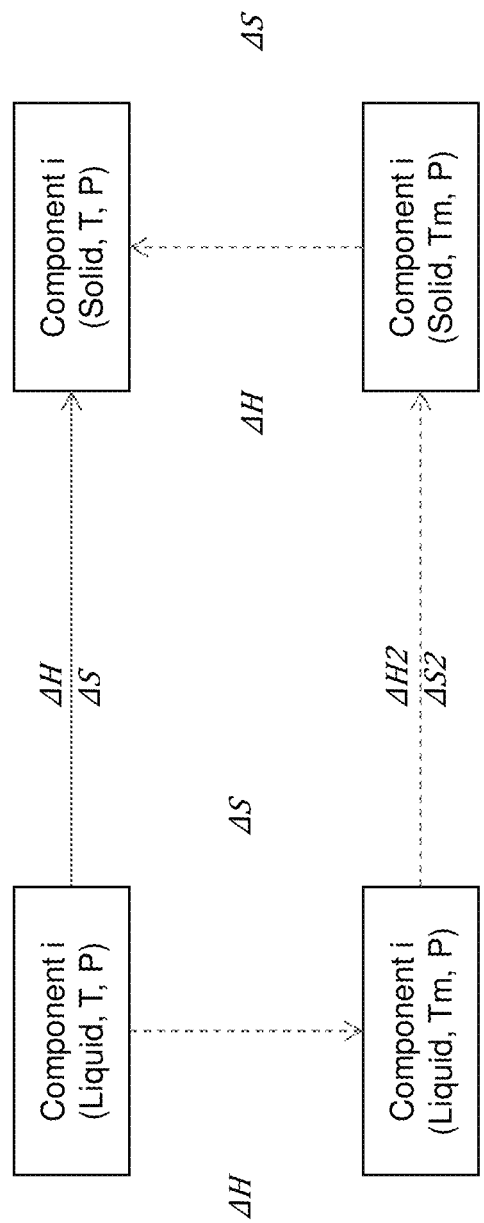
FIG. 2 is a scheme of enthalpy and entropy change for a mixture transitioning from a liquid to a solid.

The enthalpy and entropy changes are state variables in thermodynamics and can be calculated by designing a calculable route. An example of such a route is provided in FIG. 2. Therefore, at the heterogeneous phase equilibrium, there is the following relationship.

$$RT\ln(\alpha_A^1/\alpha_A^2)=\Delta H_m-T\Delta S_m \quad \text{Eq. 11}$$

To calculate the enthalpy change and entropy change for component i from liquid to solid, a new route is designed and consists of three steps. The liquid component i at temperature T and pressure P is chilled to the melting point of component i ($T_{m,i}$) and the enthalpy change and entropy change are $\Delta H_{m,i}^1(T,P)$ and $\Delta S_{m,i}^1(T,P)$. The liquid component i changes from liquid to solid at the melting point of component i, and the enthalpy change and entropy change are $\Delta H_{m,i}^2(T,P)$ and $\Delta S_{m,i}^2(T,P)$. Solid component i is heated from the melting point of component i to temperature T and the enthalpy change and entropy change are $\Delta H_{m,i}^1(T,P)$ and $\Delta S_{m,i}^1(T,P)$. The enthalpy change and entropy change in each step are shown in Eq. 11A to 11F.

$$\Delta H_{m,i}^1(T,P) = \int_T^{T_{m,i}} C_{p,m,i}^L dT \qquad \text{Eq. 11A}$$

$$\Delta S_{m,i}^1(T,P) = \int_T^{T_{m,i}} C_{p,m,i}^L / T \, dT \qquad \text{Eq. 11B}$$

$$\Delta H_{m,i}^2(T,P) = -\Delta_{fus} H_{m,i} \qquad \text{Eq. 11C}$$

$$\Delta S_{m,i}^2(T,P) = -\Delta_{fus} H_{m,i} / T_{m,i} \qquad \text{Eq. 11D}$$

$$\Delta H_{m,i}^3(T,P) = \int_{T_{m,i}}^T C_{p,m,i}^S dT \qquad \text{Eq. 11E}$$

$$\Delta S_{m,i}^3(T,P) = \int_{T_{m,i}}^T C_{p,m,i}^S / T \, dT \qquad \text{Eq. 11F}$$

Where
$C_{p,m,i}^L$: Molar heat capacity of liquid component i at constant pressure
$C_{p,m,i}^S$: Molar heat capacity of solid component i at constant pressure
$\Delta_{fus} H_{m,i}$: Molar fusion enthalpy of component i According to thermodynamic state variables, there are the following two relations as shown in Eqs. 11G and 11H.

$$\Delta H_{m,i}^\circ(T,P) = \Delta H_{m,i}^1(T,P) + \Delta H_{m,i}^2(T,P) + \Delta H_{m,i}^3(T,P) \qquad \text{Eq. 11G}$$

$$\Delta S_{m,i}^\circ(T,P) = \Delta S_{m,i}^1(T,P) + \Delta S_{m,i}^2(T,P) + \Delta S_{m,i}^3(T,P) \qquad \text{Eq. 11H}$$

According to Eqs. 11A through 11H, the enthalpy change and entropy change of component i from liquid to solid are shown in Eq. 11I and 11J.

$$\Delta H_{m,i}^\circ(T,P) = -\int_T^{T_{m,i}} \Delta C_{p,m,i} dT - \Delta_{fus} H_{m,i} \qquad \text{Eq. 11I}$$

$$\Delta S_{m,i}^\circ(T,P) = -\int_T^{T_{m,i}} (\Delta C_{p,m,i}/T) dT - \Delta_{fus} H_{m,i}/T_{m,i} \qquad \text{Eq. 11J}$$

Where
$\Delta C_{p,m,i}$: Molar heat capacity difference of component i at constant pressure in liquid and solid $$\Delta C_{p,m,i} = C_{p,m,i}^L - C_{p,m,i}^S \qquad \text{Eq. 11K}$$

According to the above equations, one thermodynamic model to predict the cloud point as the function of the composition is show in Eq. 11L.

$$RT \ln(\alpha_i^L/\alpha_i^S) = -\Delta_{fus} H_{m,i}(1 - T/T_{m,i}) - \int_T^{T_{m,i}} \Delta C_{p,m,i} dT + T \int_T^{T_{m,i}} (\Delta C_{p,m,i}/T) dT \qquad \text{Eq. 11L}$$

The heat capacity difference of component i in liquid and solid can be considered negligible and the thermodynamic model can then be expressed according to Eq. 11M.

$$RT \ln(\Delta_i^L/\Delta_i^S) = -\Delta_{fus} H_{m,i}(1 - T/T_{m,i}) \qquad \text{Eq. 11M}$$

The solid only contains one component in an ideal solution. Therefore, the thermodynamic model can be expressed according to Eq. 11N.

$$RT \ln \Delta_i^L = -\Delta_{fus} H_{m,i}(1 - T/T_{m,i}) \qquad \text{Eq. 11N}$$

According to the definition of activity (further defined herein), the thermodynamic model changes to Eq. 11O.

$$R \ln(\gamma_i^L \chi_i^L) = \Delta_{fus} H_{m,i}(1/T_{m,i} - 1/T) \qquad \text{Eq. 11O}$$

The activity coefficient of the component in the mixture of FAME can be calculated according to the Modified Universal Functional Activity Coefficient (UNIFAC) model, further described below. For a given composition of FAME, there is a calculated temperature according to Eq. 11O for each component. The cloud point of the mixture of FAME is the highest calculated temperature.

In a special case, the mixture of FAME is close to an ideal solution. The activity coefficient is 1 and the thermodynamic model becomes to Eq. 11P.

$$R \ln(\chi_i^L) = \Delta_{fus} H_{m,i}(1/T_{m,i} - 1/T) \qquad \text{Eq. 11P}$$

For a given composition of FAME, a temperature is calculated according to Eq. 11P for each component. The highest calculated temperature is the cloud point of the mixture of FAME.

Modified Universal Functional Activity Coefficient (UNIFAC) Model

As seen in Eq. 11, activities are introduced to the model. The activity of A is defined as in Eq. 12.

$$a_A = \gamma_A \chi_A \qquad \text{Eq. 12}$$

Where
$\gamma_A$: Activity coefficient of A
$\chi_A$: Mole fraction of A

When the components are independent and do not interact, the system is ideal. Therefore, the activity coefficient is 1 and the activity is equal to the molar fraction. Thus, for the ideal system, the thermodynamic model for the heterogeneous phase equilibrium is shown in Eq. 13.

$$RT \ln(\chi_A^1/\chi_A^2) = \Delta H_m - T \Delta S_m \qquad \text{Eq. 13}$$

According to the relationship between chemical potential and enthalpy/entropy, the thermodynamic model is written as $$RT \ln\left(\frac{\gamma_i^S x_i^S}{\gamma_i^L x_i^L}\right) = \Delta H_{m,i}(T, P) - T \Delta S_{m,i}(T, P) \qquad \text{Eq. 13A}$$

with $$\Delta H_{m,i} \int_T^{T_{m,i}} \Delta C_{P,m,i} \, dT + \Delta_{fus} H_{m,i} \qquad \text{Eq. 13B}$$

$$\Delta S_{m,i} = \frac{\Delta_{fus} H_{m,i}}{T_{m,i}} + \int_T^{T_{m,i}} \left(\frac{\Delta C_{P,m,i}}{T}\right) dT \qquad \text{Eq. 13C}$$

Where
$\Delta_{fus} H_{m,i}$ and $\Delta C_{p,m,i}$ are the molar fusion enthalpy of component i and the difference in the heat capacity at constant pressure between solid phase and liquid phase, respectively, and
$T_{m,i}$ is the melting point of component i.

Therefore, the thermodynamic model can be provided as $$RT \ln\left(\frac{\gamma_i^S x_i^S}{\gamma_i^L x_i^L}\right) = \int_T^{T_{m,i}} \Delta C_{P,m,i} \, dT + \Delta_{fus} H_{m,i}\left(1 - \frac{T}{T_{m,i}}\right) - T \int_T^{T_{m,i}} \left(\frac{\Delta C_{P,m,i}}{T}\right) dT \qquad \text{Eq. 13D}$$

The heat capacity at constant pressure change from solid phase to liquid phase is small enough to be neglected. Thus, the thermodynamic model can be provided as $$\ln\left(\frac{\gamma_i^S x_i^S}{\gamma_i^L x_i^L}\right) = \frac{\Delta_{fus} H_{m,i}}{R}\left(\frac{1}{T} - \frac{1}{T_{m,i}}\right) \quad \text{Eq. 13E}$$

Generally, the solid phase has small amount of fatty acid methyl esters at the cloud point. Therefore, the solid phase can be viewed as one component and an ideal solution. Consequently, the thermodynamic model is written as $$\ln(\gamma_i^L x_i^L) = \frac{\Delta_{fus} H_{m,i}}{R}\left(\frac{1}{T_{m,i}} - \frac{1}{T}\right) \quad \text{Eq. 13F}$$

This equation is used to calculate the T for different components and the maximum value of T is viewed as the cloud point.

When the mixture of fatty acid methyl esters is viewed as an ideal solution, the activity coefficient is 1 and the model is written as $$\ln(x_i^L) = \frac{\Delta_{fus} H_{m,i}}{R}\left(\frac{1}{T_{m,i}} - \frac{1}{T}\right). \quad \text{Eq. 13G}$$

However, modeling using ideal framework results in unacceptable inaccuracies. Therefore, it is necessary to know the activity coefficient in non-ideal systems for the utilization of the thermodynamic model of heterogeneous phase equilibrium. The modified UNIFAC model is the most accurate for calculating the activity coefficients. The modified UNIFAC model is derived from UNIFAC model.

To further describe the modified UNIFAC model, first the UNIFAC model is described. In the UNIFAC model, the activity coefficient has two parts: the effect of the group shape and the effect of the group interactions (as shown in Eq. 14).

$$\ln \gamma_i = \ln \gamma_i^{GS} + \ln \gamma_i^{GI} \quad \text{Eq. 14}$$

Where
$\gamma_i$: Activity coefficient of component i
$\gamma_i^{GS}$: Effect of group interaction on the activity coefficient of component i
$\gamma_i^{GI}$: Effect of group interaction on the activity coefficient of component i The effect of the group shape on the activity coefficient is expressed in Eq. 15.

$$\ln \gamma_i^{GS} = 1 - V_i + \ln V_i - 5q_i(1 - V_i/F_i + \ln(V_i/F_i)) \quad \text{Eq. 15}$$

Where $$V_i = r_i/\Sigma_j \chi_j r_j \quad \text{Eq. 16}$$

$$r_i = \Sigma_i \nu_{ki} \delta_i \quad \text{Eq. 17}$$

$$F_i = q_i/\Sigma_j \chi_j q_j \quad \text{Eq. 18}$$

$$q_i = \Sigma_i \nu_{ki} Q_i \quad \text{Eq. 19}$$

Where
$\chi_j$: Mole Fraction of component j
$\delta_k$: Volume parameter of group k
$Q_k$: Surface area parameter of group k
$\nu_{ki}$: Number of group k in component i The effect of the group interaction on the activity coefficient is shown in Eq. 20.

$$\ln \gamma_i^{GI} = \Sigma_k \nu_{ki}(\ln \eta_k - \ln \eta_k^i) \quad \text{Eq. 20}$$

ln $\eta_k$ is the group k contribution on the activity coefficient through the group interaction (as shown in Eq. 21) and ln $\eta_k^i$ is the group k contribution on the activity coefficient through the group interaction in the pure component i (as shown in Eq. 22).

$$\ln \eta_k = 5Q_k(1 - \ln(\Sigma_m \theta_m \tau_{mk}) - \Sigma_i(\theta_i \tau_{ki})/\Sigma_j \theta_j \tau_{ji}) \quad \text{Eq. 21}$$

$$\ln \eta_k^i = 5Q_k(1 - \ln(\Sigma_m \theta_m \tau_{mk}) - \Sigma_i(\theta_i \tau_{ki})/\Sigma_j \theta_j \tau_{ji})(\text{for } \chi_i = 1) \quad \text{Eq. 22}$$

Where $$\theta_m = Q_m X_m / \Sigma_n Q_n X_n \quad \text{Eq. 23}$$

$$X_m = \Sigma_j \nu_{mj} \chi_j / \Sigma_i \Sigma_j \nu_{mj} \chi_j \quad \text{Eq. 24}$$

$$\tau_m = \exp(-A_{ji}/T) \quad \text{Eq. 25}$$

Where
$A_{ji}$: Group interaction parameter

To decrease the deviation in predicting activity coefficient, the UNIFAC model was modified. According to the modified UNIFAC model, the activity coefficient includes two parts: the effect of the group shape on the activity coefficient and the effect of the group interaction on the activity coefficient. In the modified UNIFAC model, both the effects of group shape and group interaction on the activity coefficient of the modified UNIFAC model are different from those of the UNIFAC model.

According to the modified UNIFAC model, the effect of the group shape on the activity coefficient is expressed in Eq. 26.

$$\ln \gamma_i^{GS} = 1 - V_i^1 + \ln V_i^1 - 5q_i(1 - V_i/F_i + \ln(V_i/F_i)) \quad \text{Eq. 26}$$

And $$V_i^1 = r_i^{3/4}/\Sigma_j \chi_j r_j^{3/4} \quad \text{Eq. 27}$$

$$V_i = r_i/\Sigma_j \chi_j r_j \quad \text{Eq. 28}$$

$$r_i = \Sigma_i \nu_{ki} \delta_i \quad \text{Eq. 29}$$

$$F_i = q_i/\Sigma_j \chi_j q_j \quad \text{Eq. 30}$$

$$q_i = \Sigma_i \nu_{ki} Q_i \quad \text{Eq. 31}$$

Where
$\chi_j$: Molar Fraction of component j
$\delta_k$: Volume parameter of group k
$Q_k$: Surface area parameter of group k
$\nu_{ki}$: Number of group k in component i The effect of the group interaction on the activity coefficient is shown in Eq. 32.

$$\ln \gamma_i^{GI} = \Sigma_k \nu_{ki}(\ln \eta_k - \ln \eta_k^i) \quad \text{Eq. 32}$$

where, ln $\eta_k$ is the group k contribution on the activity coefficient through the group interaction (as shown in Eq. 33), ln $\eta_k^i$ is the group k contribution on the activity coefficient through the group interaction in the pure component i (as shown in Eq. 34).

$$\ln \eta_k = \frac{zQ_k}{2}\left\{-\ln\left(\sum_m \theta_m \tau_{mk}\right) + 1 - \frac{\sum_l \theta_l \tau_{kl}}{\sum_j \theta_j \tau_{jl}}\right\} \quad \text{Eq. 33}$$

-continued $$\ln \eta_k^i = \frac{zQ_k}{2}\left\{-\ln\left(\sum_m \theta_m \tau_{mk}\right) + 1 - \frac{\sum_l \theta_l \tau_{kl}}{\sum_j \theta_j \tau_{jl}}\right\} \quad \text{Eq. 34}$$

(for $x_i = 1$)
where $$\theta_m = \frac{Q_m X_m}{\sum_n Q_n X_n} \quad \text{Eq. 35}$$

$$X_m = \frac{\sum_j v_{mj} x_j}{\sum_n \sum_j v_{nj} x_j} \quad \text{Eq. 36}$$

$$\tau_{ji} = \exp\left(-\frac{A_{ji}}{T} - B_{ji} - C_{ji}T\right) \quad \text{Eq. 37}$$

where
$A_{ji}$: Group interaction parameter
$B_{ji}$: Group interaction parameter
$C_{ji}$: Group interaction parameter To apply the thermodynamic model disclosed herein to predict the cloud point according to the composition of fatty acid methyl esters, the properties of pure fatty acid methyl esters such as melting points and fusion enthalpy should be known. To use the modified UNIFAC model in activity coefficients prediction, the group shape parameters and group interaction parameter should be known. These parameters are discussed below.

Parameters
Melting Points and Fusion Enthalpy

To predict the cloud point based on the composition of fatty acid methyl esters by the above thermodynamic model, the melting points and fusion enthalpies of the pure components should be known. The relationship between melting point and fusion enthalpy as shown in Eq. 38.

$$\Delta_{fus}H_m = T_m \Delta_{fus}S_m \quad \text{Eq. 38}$$

The fusion enthalpy and fusion entropy can be calculated by a group contribution model according to Eq. 39.

$$\Delta_{fus}S_m = \sum_i n_i \kappa_i \quad \text{Eq. 39}$$

Where $n_i$ is the number of group i in the component, and $\kappa_i$ is the group value of entropy contribution, respectively.

According to the group contribution model, the fatty acid methyl esters have the following groups: —CH$_3$, —CH$_2$—CH= and —C(=O)O—. The group contributions for fusion enthalpy are shown in Table 2.

TABLE 2

Group values for the fusion entropy contributions

| Group | CH$_3$— | —CH$_2$— | —CH= | —(C=O)O— |
|---|---|---|---|---|
| Group Values J · mol$^{-1}$ · K$^{-1}$ | 17.6 | 7.1$^a$ | 5.3 | 7.7 |

$^a$The group value will multiply 1.31 for the number of consecutive methylene groups no less than the sum of the remaining groups.

The melting points of fatty acid methyl esters are shown in Table 1. The fusion enthalpies of fatty acid methyl esters are shown in Table 3.

TABLE 3

Fusion enthalpies of fatty acid methyl esters

| Components | C16:0 | C16:1 | C18:0 | C18:1 | C18:2 | C18:3 |
|---|---|---|---|---|---|---|
| $\Delta_{fus}H_{m,i}$ (experimental) | 55350 | — | 64430 | 43890 | — | — |
| $\Delta_{fus}H_{m,i}$ (predicted) | 52480 | 43733 | 59844 | 46507 | 41846 | 37089 |

The fusion enthalpies of the saturated pure fatty acid methyl esters were determined. Due to the non-ideal property of the mixture of fatty acid methyl esters, the activity coefficients of the components are determined. For the methyl esters, according the modified UNIFAC model, the groups include CH$_2$, CH$_3$, CH=CH and (C=O)OCH$_3$. The group shape parameters are shown in Table 4 and the group interaction parameters are shown in Table 5. Based on the composition of fatty acid methyl esters and the group parameter, above equations can be used to predict the activity coefficients.

TABLE 4

Group Shape parameters in the modified UNIFAC model

|  | CH$_3$ | CH$_2$ | CH=CH | (C=O)OCH$_3$ |
|---|---|---|---|---|
| $\delta_k$ | 0.6325 | 0.6325 | 1.2832 | 1.2700 |
| $Q_k$ | 1.0608 | 0.7081 | 1.2489 | 1.6286 |

TABLE 5

Group interaction parameters in the modified UNIFAC model

|  |  | CH2/CH3 | CH=CH | (C=O)OCH$_3$ |
|---|---|---|---|---|
| CH2/CH3 | A | 0 | 189.66 | 98.656 |
|  | B | 0 | −0.2723 | 1.9294 |
|  | C | 0 | 0 | 3.133 × 10$^{-3}$ |
| CH=CH | A | −95.418 | 0 | 980.74 |
|  | B | 6.171 × 10$^{-2}$ | 0 | −2.4224 |
|  | C | 0 | 0 | 0 |
| (C=O)OCH$_3$ | A | 632.22 | −582.82 | 0 |
|  | B | −3.3912 | 1.6732 | 0 |
|  | C | 3.928 × 10$^{-3}$ | 0 | 0 |

Results
Cloud Points of a Binary System

Figures 3A, 3B, 3C, 3D:
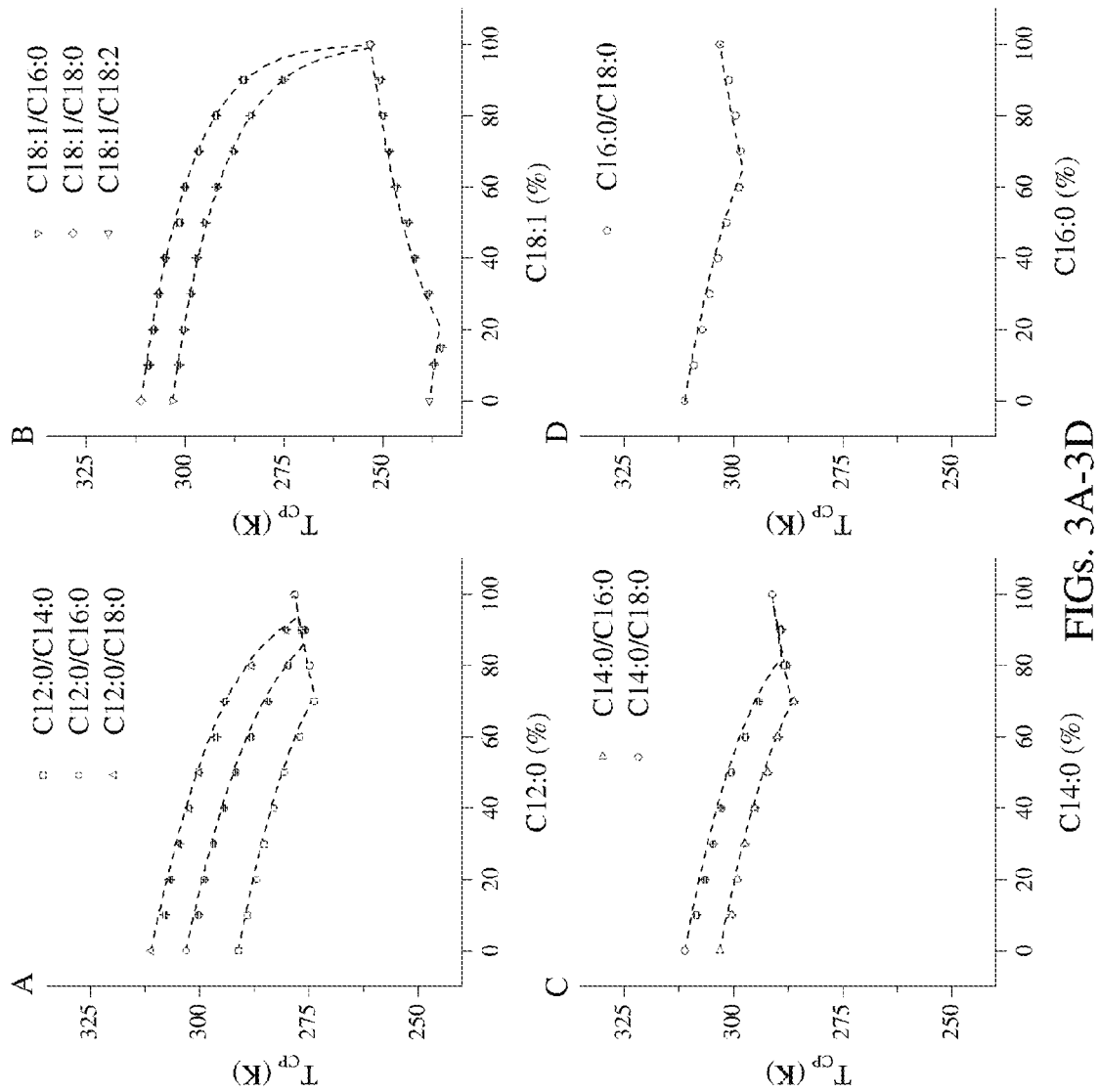
FIGS. 3A-3D are plots of cloud point for various binary mixtures of fatty acid methyl esters.

The model was tested for several binary FAME and the measured and predicted cloud points of these binary mixtures are shown in FIG. 3. For the binary mixture of saturated FAME components, there are eutectic points (see FIGS. 3A, 3C and 3D). For example, in the case of the mixture of C12:0/C14:0, the cloud point of the mixture decreased to the eutectic point (approximately. 70% of C12:0). Binary mixtures of C12:0/C16:0, C12:0/C18:0, C14:0/C16:0, C14:0/C18:0/and C16:0/C18:0 showed similar behavior (see FIGS. 3A, 3C and 3D). Binary mixtures of saturated/unsaturated FAME components, such as the mixtures of C18:1/C16:0 and C18:1/C18:0 did not show eutectic compositions (see FIG. 3B). The cloud points of these binary systems increased sharply with the fraction of the saturated FAME when the fraction of C18:1 is larger than 80%. For the binary mixture of C18:1/C18:2, there is also eutectic point.

Cloud Points and the Compositions in Ternary System

Figure 4:
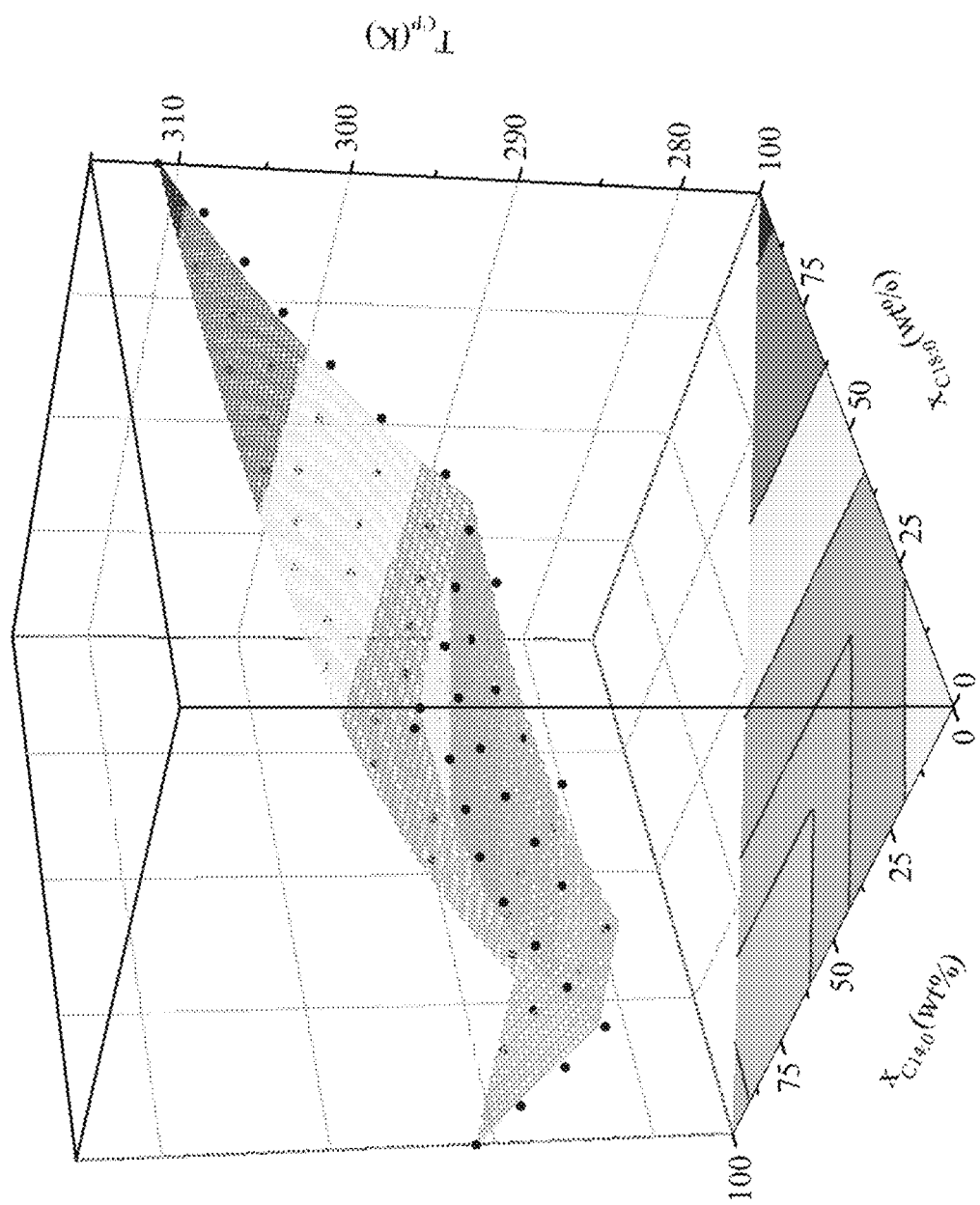
FIG. 4 is a plot of cloud points of a ternary mixture of C14:0/C16:0/C18:0.
Figure 5:
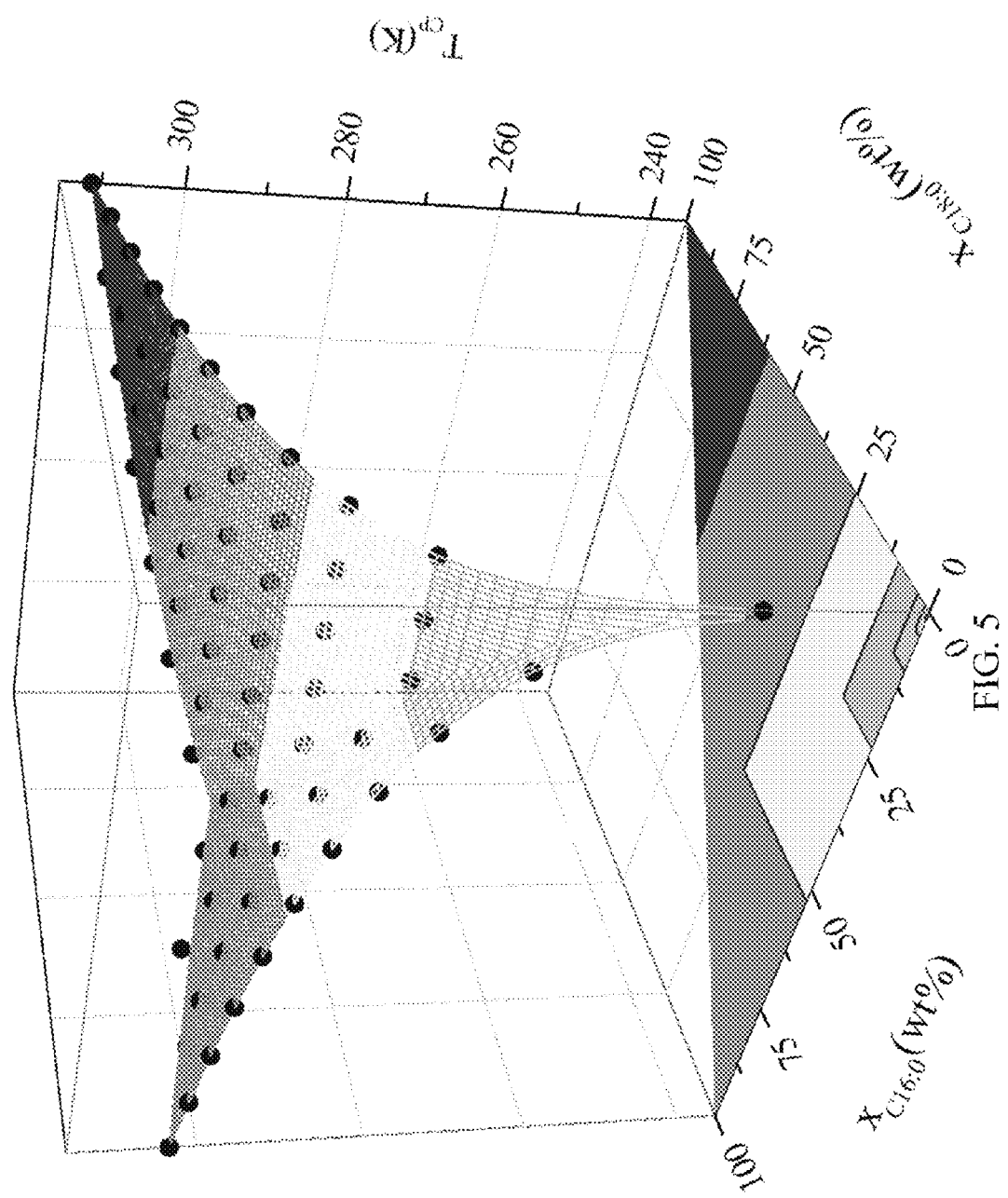
FIG. 5 is a plot of cloud points of a ternary mixture of C16:0/C18:0/C18:1.
Figure 6:
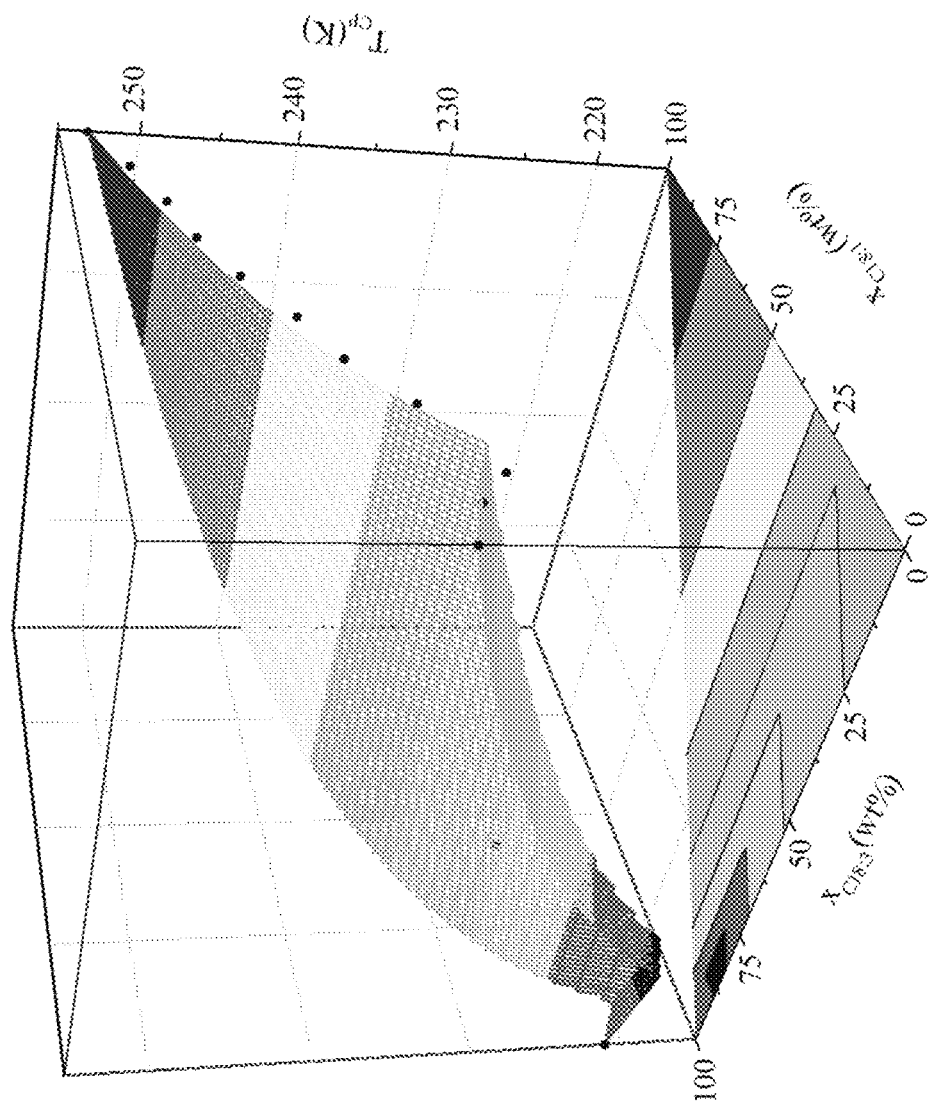
FIG. 6 is a plot of cloud points of a ternary mixture of C18:1/C18:2/C18:3.

Ternary systems were examined composed of: C14:0/C16:0/C18:0, C18:/C18:2/C18:3 and C16:0/C18:0/C18:1. The predicted and experimentally measured cloud points of these ternary mixtures are presented in FIGS. 4, 5, and 6. The surfaces of these figures consist of the predicted cloud points and the balls in these figures are the measured cloud points. The ternary mixtures of C14:0/C16:0/C18:0 and C18:1/C18:2/C18:3 have a ternary eutectic point (FIGS. 4 and 6). The cloud point of the mixture at the ternary eutectic point is lowest. The ternary mixture of C16:0/C18:0/C18:1 does not have a ternary eutectic point (FIG. 5).

Figure 7:
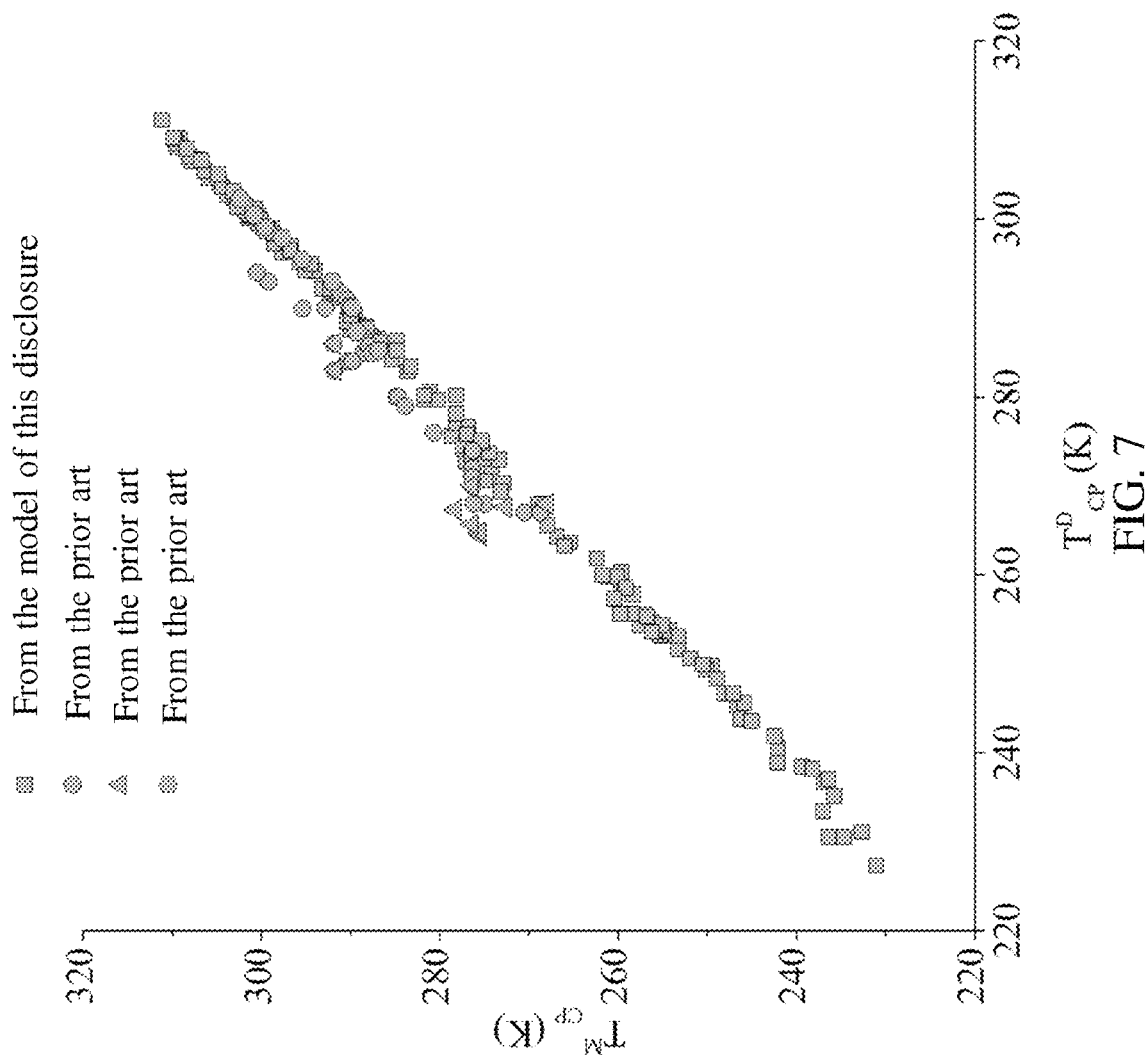
FIG. 7 is a plot of predicted cloud points vs. detected cloud points for the method according to the present disclosure and the methods presented in the prior art.

Using method discussed in the present disclosure, the predicted and experimentally measured cloud points are plotted in FIG. 7. The correlation of the predicted and measured cloud points depicts a good correlation with a linear relationship (Eq. 40) with $R^2$ as high as 0.99 between predicted and detected cloud point.

$$T_{CP,P} = 0.975 T_{CP,D} + 8.55 \quad \text{Eq. 40}$$

Where $T_{CP,P}$ and $T_{CP,D}$ are the predicted cloud points and detected cloud points of the mixtures of FAME, respectively.

In operation, referring back to FIG. 1, the cloud point modeling unit 120 can include an application specific integrated circuit or a computer. In each case, a memory (not shown) can be used to hold both i) executable software code prepared from a source code and ii) scratchpad memory for necessary calculations. A software implementation using NetBeans IDE compiler and a package from e j technologies for compiling and packaging the software for modeling cloud point based on the method disclosed herein is provided in Appendix-A, filed herewith, entirety of which is incorporated herein by reference.

Figure 8:
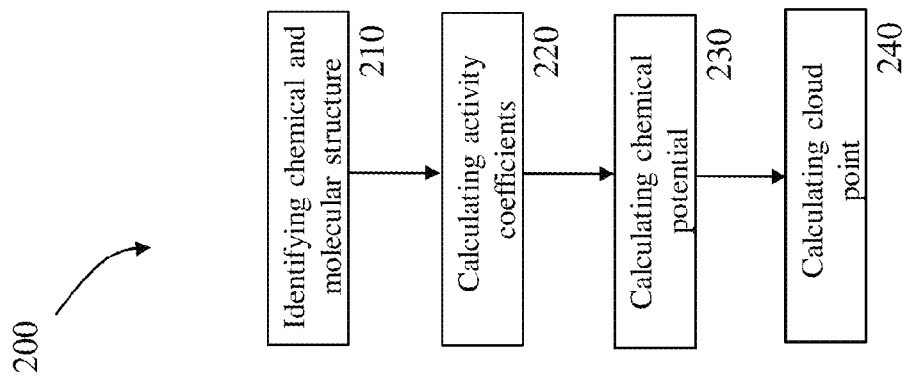
FIG. 8 is a flow chart of a method according to the present disclosure.

The method described herein is depicted in FIG. 8. The method 200 is for predicting onset of liquid phase to solid phase transition of a mixture including a plurality of fatty acid methyl esters components. The method 200 includes: identifying chemical and molecular structure of each component of the mixture (step 210). The method 200 also includes calculating activity coefficients for each component in a liquid phase and a solid phase according to $$\ln\gamma_i^{GS} = 1 - V_i' + \ln V_i' - 5q_i\left(1 - \frac{V_i}{F_i} + \ln\left(\frac{V_i}{F_i}\right)\right)$$

and $$\ln\gamma_i^{GL} = \sum_k v_{ki}(\ln\eta_k - \ln\eta_k^j)$$

(step 220). The method 200 also includes:
calculating chemical potential for each component in the liquid phase and in the solid phase at a predetermined temperature and a predetermined pressure according to $$\mu_i^L = \mu_i^{0,L}(T,P) + RT\ln(\gamma_i^L \chi_i^L)$$

$$\mu_i^S = \mu_i^{0,S}(T,P) + RT\ln(\gamma_i^S \chi_i^S)$$

(step 230). The method 200 also includes calculating the cloud point of the mixture (step 240).

Those skilled in the art will recognize that numerous modifications can be made to the specific implementations described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

The invention claimed is:

1. A method for predicting onset of liquid phase to solid phase transition of a mixture including a plurality of fatty acid methyl esters (FAME) components, the FAME components are subdivided into a plurality of groups, comprising:
identifying chemical and molecular structure of each component of the mixture using data collected with a mass spectrometer and using a computing device containing a library of information of the chemical and molecular structure of each component;
calculating, using the computing device, activity coefficients for each component in a solid phase and a liquid phase according to $$\ln\gamma_i^{GS} = 1 - V_i' + \ln V_i' - 5q_i\left(1 - \frac{V_i}{F_i} + \ln\left(\frac{V_i}{F_i}\right)\right)$$

and $$\ln\gamma_i^{GL} = \sum_k v_{ki}(\ln\eta_k - \ln\eta_k^j),$$

wherein:
$\gamma_i^{GS}$ is the effect of group interaction on the activity coefficient of component i in the solid phase;
i is the ith component in the mixture;
$V_i' = r_i^{3/4}/\Sigma_j \chi_j r_j^{3/4}$, wherein:
$r_i = \Sigma_i v_{ki}\delta_i$ is the volume parameter for component i;
$v_{ki}$ is the number of a kth group in component i;
$\delta_i$ is a volume parameter of component i;
$r_j = \Sigma_j v_{kj}\delta_j$, is the volume parameter for component j;
$v_{kj}$ is the number of the kth group in component j;
$\delta_j$ is a volume parameter of component j;
$\chi_j$ is the mole fraction of component j;

$q_i = \Sigma_i v_{ki} Q_i$ is the area parameter, wherein:
$v_{ki}$ is the number of the kth group in component i
$Q_i$: is the surface area parameter of component i;

$V_i = r_i/\Sigma_j \chi_j r_j;$ $F_i = q_i/\Sigma_j \chi_j q_j;$ $\gamma_i^{GL}$ is the effect of group interaction on the activity coefficient of component i in the liquid phase;
$\ln\eta_k$ is the kth group contribution on the activity coefficient through the group interaction;
$\ln\eta_k$ is the kth group contribution on the activity coefficient through the group interaction in the pure component i;
calculating, using the computing device, chemical potential (μ) for each component in the liquid phase (L) and in the solid phase (S) at a predetermined temperature (T) and a predetermined pressure (P) according to $$\mu_i^L = \mu_i^{0,L}(T,P) + RT\ln(\gamma_i^{GL}\chi_i^L) \text{ and}$$

$$\mu_i^S = \mu_i^{0,S}(T,P) + RT\ln(\gamma_i^{GS}\chi_i^S), \text{ wherein}$$

$\mu_i^L$ is the chemical potential of component i in the liquid phase;
$\mu_i^{0,L}$ is the chemical potential of component i in the liquid phase at temperature T and pressure P;
R is the ideal gas constant;
$\gamma_i^{GL}$ is the effect of group interaction on the activity coefficient of component i in the liquid phase;
$\chi_i^L$ is the mole fraction of component i in the liquid phase;
$\mu_i^S$ is the chemical potential of component i in the solid phase;

$\mu_i^{0,S}$ is the chemical potential of component i in the solid phase at temperature T and pressure P;

$\gamma_i^{GS}$ is the effect of group interaction on the activity coefficient of component i in the solid phase;

$x_i^S$ is the mole fraction of component i in the solid phase; and calculating, using the computing device, the cloud point of the mixture, wherein the cloud point is used to characterize cold flow properties of FAME, according to $$RT\ln\left(\frac{\gamma_i^{GS} x_i^S}{\gamma_i^{GL} x_i^L}\right) = \mu_i^{0,L}(T,P) - \mu_i^{0,S}(T,P),$$

wherein $q_i = \Sigma v_{ki} Q_k$, wherein $Q_k$ is the surface area parameter of the kth group, $$\ln \eta_k = \frac{zQ_k}{2}\left\{-\ln\left(\sum_m \theta_m \tau_{mk}\right) + 1 - \frac{\sum_l \theta_l \tau_{kl}}{\sum_j \theta_j \tau_{jl}}\right\},$$

wherein z is the charge of the *kth* group, $$\ln \eta_k^j = \frac{zQ_k}{2}\left\{-\ln(\Sigma_m \theta_m \tau_{mk}) + 1 - \frac{\Sigma_l \theta_l \tau_{kl}}{\Sigma_j \theta_j \tau_{jl}}\right\},$$

$$\theta_m = \frac{Q_m X_m}{\sum_n Q_n X_n}, \; \theta_l = \frac{Q_l X_l}{\Sigma_j Q_n X_n}, \; \theta_j = \frac{Q_j X_j}{\Sigma_j Q_n X_n},$$

wherein $Q_m$ is the surface area parameter of the mth group, $Q_n$ is the surface area of the nth group, $Q_l$ is the surface area parameter of the lth group, and $Q_j$ is the surface area parameter of component j, $$X_m = \frac{\Sigma_j v_{mj} x_j}{\Sigma_n \Sigma_j v_{nj} x_j}, \text{ wherein:}$$

$v_{mj}$ is the number of a *mth* group in component *j*;

and $v_{nj}$ is the number of a *nth* group in component *j*;

$$X_n = \frac{\Sigma_j v_{nj} x_j}{\Sigma_n \Sigma_j v_{nj} x_j}, \text{ wherein:}$$

$$X_l = \frac{\Sigma_j v_{lj} x_j}{\Sigma_l \Sigma_j v_{lj} x_j}, \text{ wherein:}$$

$v_{lj}$ is the number of a *lth* group in component *j*; $X_j = \frac{\Sigma_n v_{nj} x_j}{\Sigma_j \Sigma_j v_{nj} x_j}$; and $$\tau_{mk} = \exp\left(-\frac{A_{mk}}{T} - B_{mk} - C_{mk}T\right);$$

$$\tau_{kl} = \exp\left(-\frac{A_{kl}}{T} - B_{kl} - C_{kl}T\right);$$

$$\tau_{jl} = \exp\left(-\frac{A_{jl}}{T} - B_{jl} - C_{jl}T\right), \text{ and}$$

wherein group shape parameters $\delta_k$ and $Q_k$ and group interaction parameters A, B, and C are determined from the library of information for each type of bond for each component of the mixture.

\* \* \* \* \*